(12) United States Patent
Ajami

(10) Patent No.: US 6,740,305 B1
(45) Date of Patent: May 25, 2004

(54) ASSESSMENT OF GASTRIC EMPTYING DISORDERS

(75) Inventor: Alfred M. Ajami, Brookline, MA (US)

(73) Assignee: Xanthus Life Scienes, Inc., Cambridge, MA (US)

( * ) Notice: Subject to any disclaimer, the term of this patent is extended or adjusted under 35 U.S.C. 154(b) by 0 days.

(21) Appl. No.: 09/958,438

(22) PCT Filed: Apr. 10, 2000

(86) PCT No.: PCT/US00/09477

§ 371 (c)(1),
(2), (4) Date: Oct. 9, 2001

(87) PCT Pub. No.: WO00/61197

PCT Pub. Date: Oct. 19, 2000

Related U.S. Application Data

(60) Provisional application No. 60/128,516, filed on Apr. 9, 1999.

(51) Int. Cl.⁷ .............................................. A61K 49/00
(52) U.S. Cl. .................. 424/9.1; 424/9.2; 424/1.81
(58) Field of Search ...................... 424/9.1, 9.2, 1.81; 436/181, 56, 133, 173, 900

(56) References Cited

U.S. PATENT DOCUMENTS

| | | | | |
|---|---|---|---|---|
| 5,707,602 A | * | 1/1998 | Klein | 424/1.11 |
| 6,071,245 A | * | 6/2000 | Kohno et al. | 600/532 |
| 6,432,382 B1 | * | 8/2002 | Mehta | 424/9.1 |
| 6,548,043 B1 | | 4/2003 | Wagner et al. | |

FOREIGN PATENT DOCUMENTS

| | | | | |
|---|---|---|---|---|
| WO | WO 00/00636 | 1/2000 | ............ | C12Q/1/00 |

OTHER PUBLICATIONS

B.D. Maes et al., "Combined Carbon–13–Glycine/Carbon–14–Octanoic Acid Breath Test to Monitor Gastric Emptying Rates of Liquids and Solids", The Journal of Nuclear Medicine, vol. 35, No. 5, pp. 824–831 (1994).

Naomi K. Fukagawa et al., "L–2–'13C!oxo-thiazolidine–4–carboxylic acid: a probe for precursor mobilization for glutathione synthesis", Database Chemabs 'Online! Chemical Abstracts Service, Columbus, Ohio, US, retrieved from STN Database accession No. 132:290669 XP002143974 abstract & AM. J. Physiol. (2000), 278 (1,PT. 1), E171–E176.

B. Braden et al., "The '13C!acetate breath test accurately reflects gastric emptying of liquids in both liquid and semisolid test meals", Database Embase 'Online! Elsevier Science Publishers, Amsterdam, NL, retrieved from STN Database accession No. 95102101 XP002143975 abstract &Gastroenterology, (1995) 108/4 (1048–1055).

\* cited by examiner

*Primary Examiner*—Michael G. Hartley
(74) *Attorney, Agent, or Firm*—Ogilvy Renault; France Côté; Christian Cawthorn

(57) ABSTRACT

Methods of measuring gastric emptying time comprising providing to a patient a meal comprising a breath test food additive substrate, wherein the substrate is a linear or cyclic acyl aminoacid peptidomimetic that includes a radioactive or non-radioactively labeled carbon atom; having the patient digest the meal so that the carbon labeled nutrients therein are absorbed in the small intestine and metabolized to labeled $CO_2$; and, at periodic intervals, detecting the level of labeled $CO_2$ in breath samples taken from the patient to determine the rate of gastric emptying are disclosed.

4 Claims, 7 Drawing Sheets

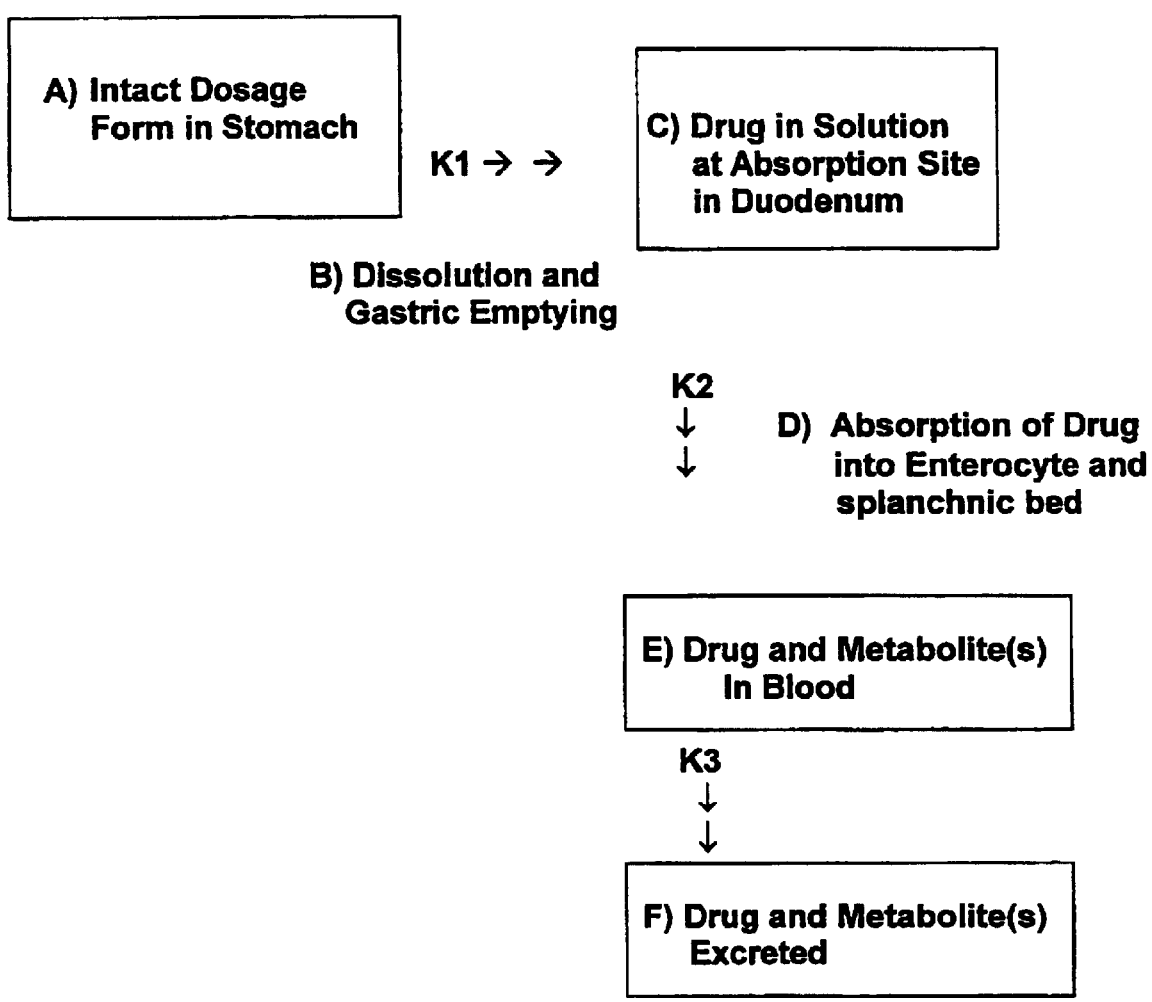

FIGURE 2: Linear acyl aminoacid peptidomimetic probes

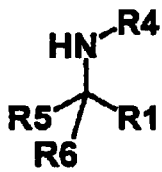

R1 = carboxyl, carboxylamide, and ketone functional groups described in Table I, with characteristic reversible subfunctionalities, including as preferred:

R2 = H, methyl, ethyl, propyl, butyl, pentyl, hexyl, isopropyl, isobutyl, sec-butyl tert-butyl, isopentyl, isohexyl, phenyl, phenylmethyl, etc.; * may be labeled at the 1-position of the alcohol chain if an ester substituent; or R3 = H, methyl, ethyl, propyl, butyl, pentyl, hexyl, isopropyl, isobutyl, sec-butyl tert-butyl, isopentyl, isohexyl, phenyl, phenylmethyl, etc.; or

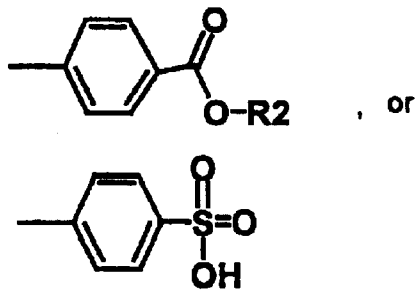

R4 = H, formyl, acetyl, benzoyl, benzyloxycarbonyl, t-butoxycarbonyl, butyryl, ethoxycarbonyl, hippuryl, isopropyloxycarbonyl, methoxyacetyl, methoxycarbonyl, pivaloyl, propionyl, etc.; * label may be positioned on the acyl carbonyl R5 = H, methyl, ethyl, propyl, butyl, pentyl, hexyl, isopropyl, isobutyl, sec-butyl tert-butyl, isopentyl, isohexyl, phenyl, phenylmethyl, etc.;

R6 = H, if R5 ≠ H; CH2-OH, CH2-SH, CH2-CH2-OH, CH2-CH2-S-CH3, CH2-COOR2, CH2-CH2-COOR2, CH2-CH2-CH2-COOR3, CH2-CH2-CON-R3, CH2-CH2-CH2-NH2, or CH2-CH2-CH2-CH2-NH2

* = Preferred position of isotopic release tag in tracer core

FIGURE 3: Cyclic acyl aminoacid peptidomim tic probes

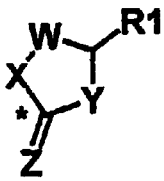

R1 = carboxyl and carboxylamide functional groups described in Table I, with characteristic reversible subfunctionalities, including as preferred:

where:

R2 = H, methyl, ethyl, propyl, butyl, pentyl, hexyl, isopropyl, isobutyl, sec-butyl tert-butyl, isopentyl, isohexyl, phenyl, phenylmethyl; and R3 = H, methyl, ethyl, propyl, butyl, pentyl, hexyl, isopropyl, isobutyl, sec-butyl tert-butyl, isopentyl, isohexyl, phenyl, phenylmethyl,

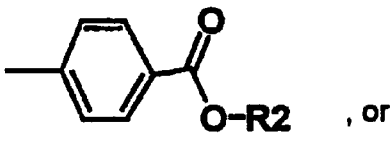 , or

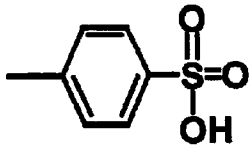

W = CH2, CH-alkyl, CH-aryl, CH2CH2, CH2-CH-alkyl, CH2-CH-aryl

X = N, O, S

Y = N, N-CH₃; and

Z = N, O, S

* = Preferred position of isotopic release tag in tracer core

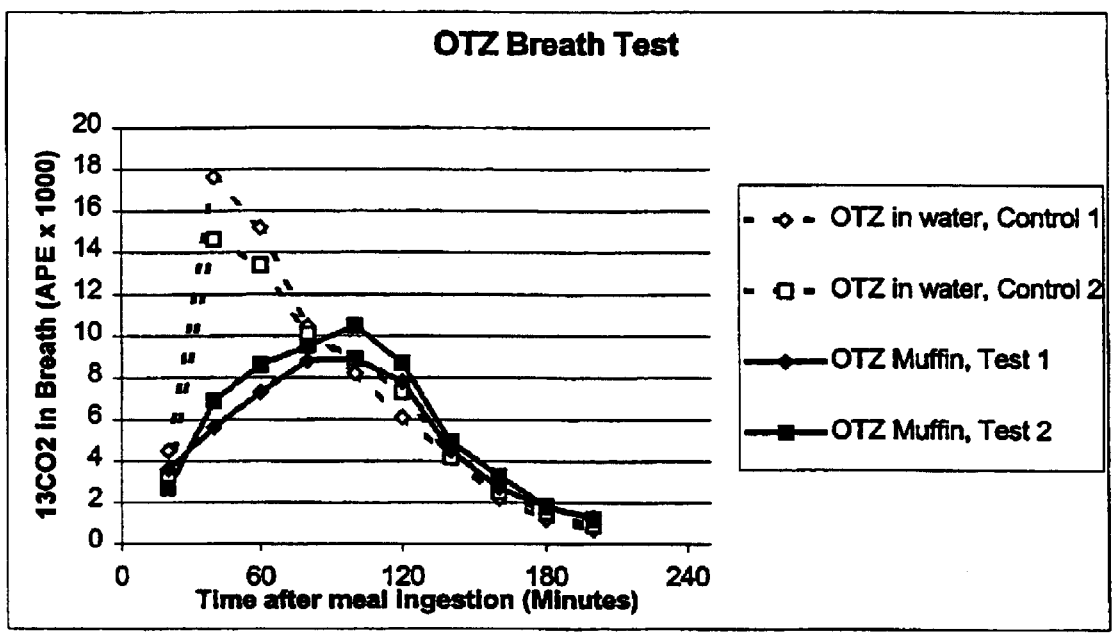
FIGURE 4: OTZ as solid phase emptying prob

FIGURE 5: OTZ as liquid phase emptying probe
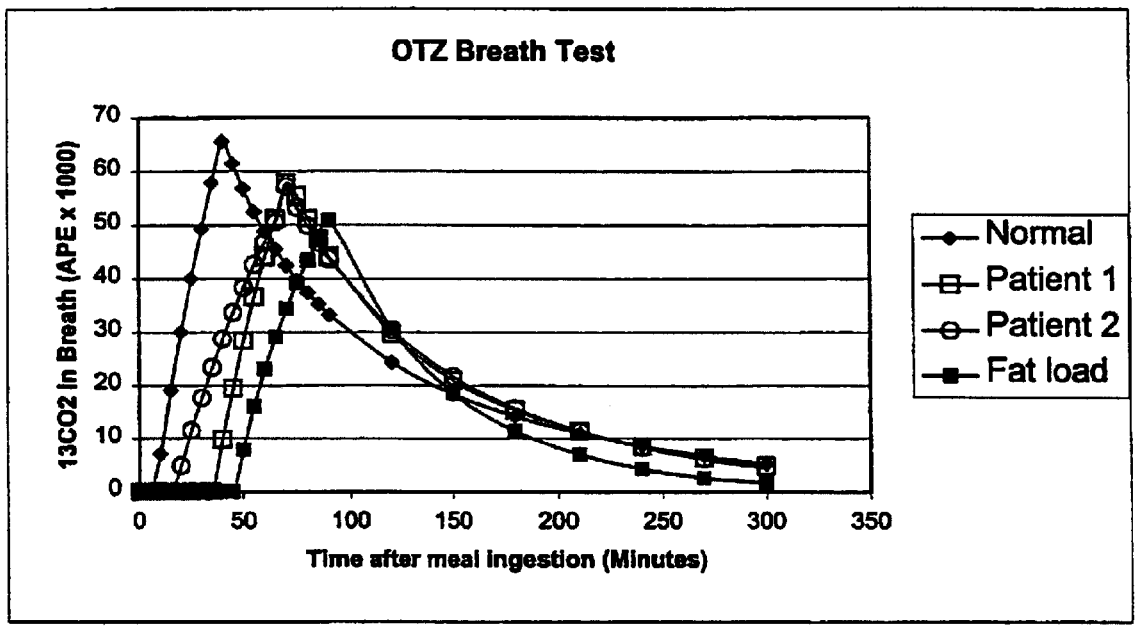

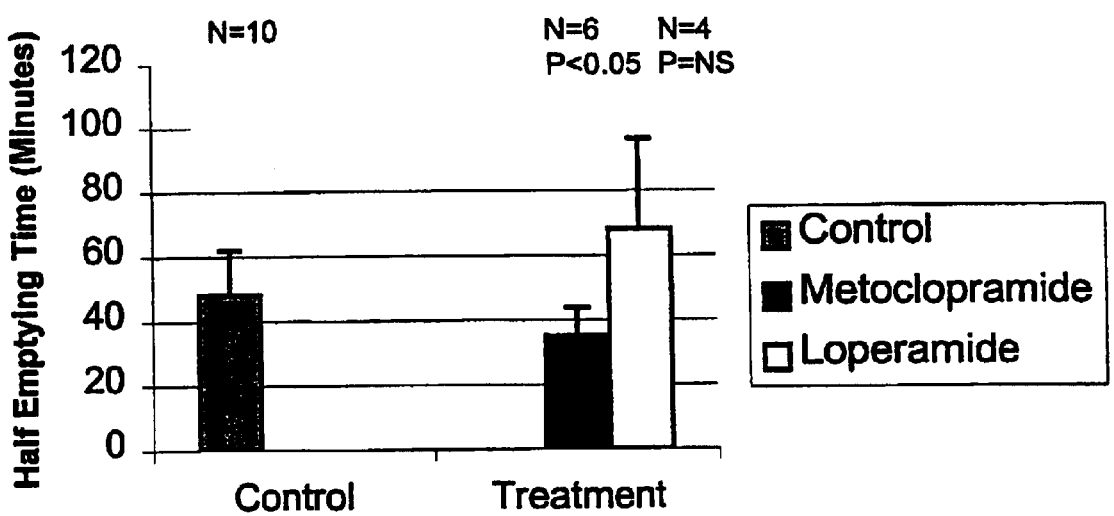
FIGURE 6: Acyl[13C]-Leucine as liquid phase emptying probe Effect of motility regulator drugs

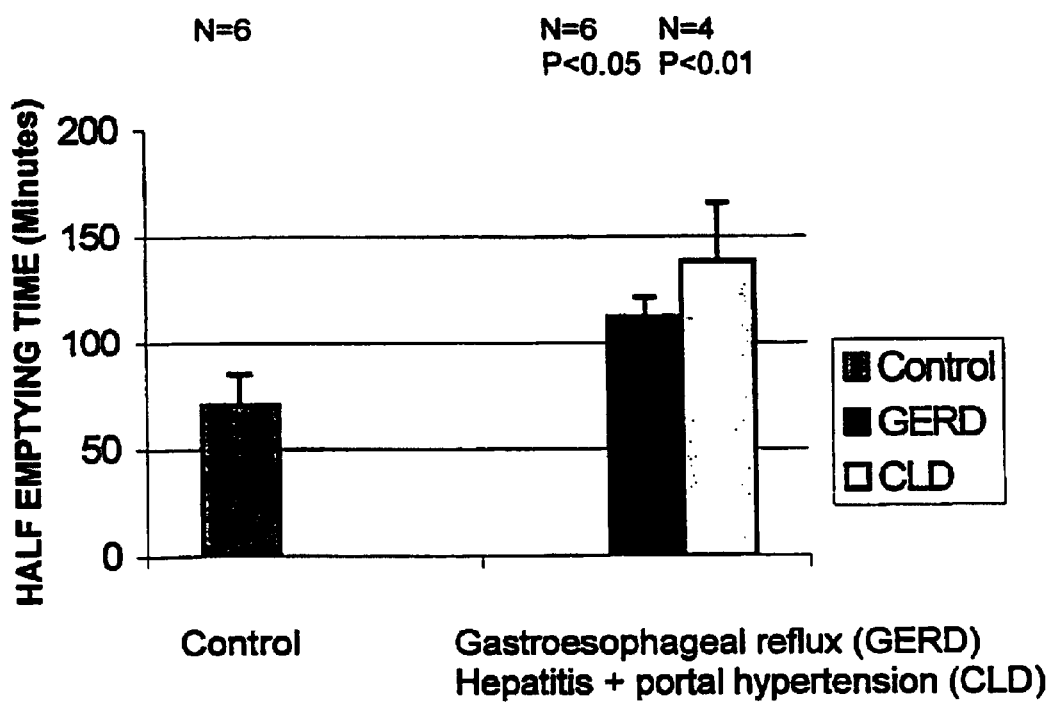

ASSESSMENT OF GASTRIC EMPTYING DISORDERS

CROSS REFERENCE TO RELATED APPLICATIONS

This application claims the priority of U.S. Provisional Patent Application No. 60/128,516 filed, Apr. 9, 1999 entitled TEST FOR GASTRIC EMPTYING, the whole of which is hereby incorporated by reference herein.

BACKGROUND OF THE INVENTION

Gastric emptying plays a major role in many diseases that impair the highly coordinated physiological response to the presence of food and digestive fluids in the stomach. The most common pathophysiological causes for gastric emptying dysregulation are acid-peptic related diseases; gastritis; metabolic, endocrine or neurological disorders; obstructions; adverse responses to drugs and surgery; exercise and a variety of rare or idiopathic conditions. These disorders are significant in terms of morbidity, and their incidence will increase with the aging population and the expected presentation of more cases of diabetes, obesity, gastric surgery, and chronic liver disease.

Improved diagnostic approachs are needed for the assessment of gastric emptying disorders. New medications make gastric disorders more treatable than in the past, but empirical trials of these drugs are expensive, and a high degree of placebo effect exists in the population. The gold standard diagnostic method for gastric emptying is scintigraphy, assessed as liquid or solid emptying. This method is of limited availability at the patient bedside or in a physician's office. It is also expensive and, furthermore, includes the use of radioactively labeled foods and imaging technology not suitable for follow-up testing or for all patient candidates (e.g., fertile women, pregnant women and children). For drug development or in other research settings where consistency is important, scintigraphy is problematic because medical centers have not converged on a single, uniform protocol. For these reasons, other non-invasive techniques such as ultrasonography, electrogastrography, magnetic resonance imaging and tomography of swallowed radiopaque markers have been proposed or are being developed as validated alternatives to nuclear medicine methodologies, but these are equally problematic and logistically complex procedures for delivery at the point of patient care.

Recently, breath tests with stable isotopes have been developed to reliably assess gastric emptying by tracking the absorption and disposition of metabolizable foods that have been tagged with non-radioactive $^{13}C$. Applicable to both the emptying of liquid and solid foods, the principal advantage of breath test technology in general is that no radiation is required and specific implementations of emptying test protocols can be performed without biological hazard and without complex equipment at the point of patient care. In practice, however, currently available diagnostic methods still involve inconveniently slow breath test protocols or expensive breath test substrates (labeled algae formulations) that may limit general clinical use.

For example, the use of octanoic acid is controversial in the medical literature and the results are highly setting dependent. The pure acid is oily, difficult to dispense in unit doses, and has a strong and disagreeable taste. The octanoic acid sodium salt is a dry powder, thus easier to divide into unit doses, and has a more acceptable taste. However, with either the free octanoic acid or its sodium salt, the test takes up to four hours and requires multiple breath samples because the pharmacokinetic modeling analysis requires several hours of post emptying data. In addition, if octanoic acid or its salt is used for Ad gastric emptying, the substrate material partitions out of the solid phase in a test meal, which can affect consistency of results. Octanoic acid is a surfactant and does not adsorb strongly to protein in the test meal. More importantly, this material is absorbed from the small intestine by a complex route and is then transported to and metabolized in various other sites within the body beyond the enterocytes and the splanchnic bed, e.g. heart, muscle and kidney. Because, in effect, gastric emptying is not the rate-limiting step in the delivery of labeled $CO_2$ to the breath during the post-absorptive fate of octanoate, the use of this and related substrates in a breath test is prone to misinterpretation attributable to confounding metabolic factors.

Therefore, there is a need for new breath test substrates that are inexpensive to manufacture and deliver compared with alternatives in radiology and nuclear medicine, perform well in liquid or solid phase emptying trials, are rapidly metabolized to allow for a faster trial completion and can be applied under a variety of physiological and metabolic conditions.

SUMMARY OF THE INVENTION

The invention is directed to the use of various linear and cyclic acyl aminoacid peptidomimetics as gastric emptying probes. The physical and biochemical properties of the probes described herein render them more suitable in methods of measuring gastric emptying time than those compositions known in the prior art. The linear and cyclic acyl aminoacid peptidomimetics useful in the method of the invention are preferably selected from the group consisting of:

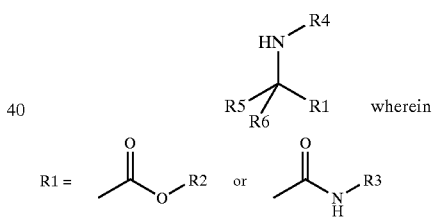

where
R2=H, methyl, ethyl, propyl, butyl, pentyl, hexyl, isopropyl, isobutyl, sec-butyl tert-butyl, isopentyl, isohexyl, phenyl, phenylmethyl; and
R3=H, methyl, ethyl, propyl, butyl, pentyl, hexyl, isopropyl, isobutyl, sec-butyl tert-butyl, isopentyl, isohexyl, phenyl, phenylmethyl,

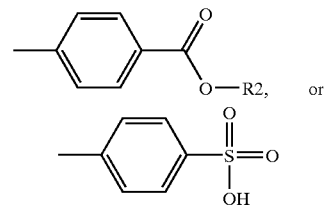

R4=H, formyl, acetyl, benzoyl, benzyloxycarbonyl, t-butoxycarbonyl, butyryl, ethoxycarbonyl, hippuryl, isopropyloxycarbonyl, methoxyacetyl, methoxycarbonyl, pivaloyl, proplonyl;

R5=H, methyl, ethyl, propyl, butyl, pentyl, hexyl, isopropyl, isobutyl, sec-butyl tert-butyl, isopentyl, isohexyl, phenyl, phenylmethyl; and R6=H, If R5≠H; CH2-OH, CH2-SH, CH2-CH2-OH, CH2-CH2-S—CH3, CH2-COOR2, CH2-CH2-COOR2, CH2-CH2-CH2-COOR3, CH2-H2-CON—R3, CH2-CH2-CH2-NH2, or CH2-CH2-CH2-CH2-NH2 and

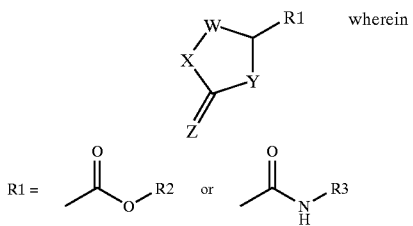 wherein where:

R2=H, methyl, ethyl, propyl, butyl, pentyl, hexyl, isopropyl, isobutyl, sec-butyl tert-butyl, isopentyl, isohexyl, phenyl, phenylmethyl; and R3=H, methyl, ethyl, propyl, butyl, pentyl, hexyl, isopropyl, isobutyl, sec-butyl tert-butyl, isopentyl, isohexyl, phenyl, phenylmethyl,

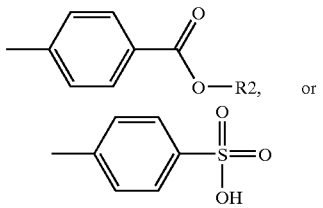

W=CH2, CH-alkyl, CH-aryl, CH2CH2, CH2-CH-alkyl, CH2-CH-aryl

X=N, O, S

Y=N, N—CH$_3$; and

Z=N, O, S.

Three requisite properties differentiate the compounds of this invention from other substances in the current practice of breath tests for gastric emptying:

1) Their adsorptive and bulk-phase behavior as aminoacids and as polyfunctional, nitrogen containing derivatives in contrast to fatty acids, permits them to bind tightly, both ionically and electrostatically, to polar and non-polar constituents of foods, in particular with protein. These properties, commonly understood to be the hallmark of amphiphilic molecules, insure that the compounds of this invention will remain tightly crosslinked to the solid phase of foods during the emptying process from the stomach and, therefore, not partition into the liquid phase thereby causing measurement error;

2) The facility for rapid absorption by and rapid transport through the mucosa of the small intestine is a further requisite property embodied in the compounds of this invention. Acyl aminoacids and their peptidomimetic derivatives are essential nutrients whose rapid absorption has been a focus of the evolution of the digestive system of carnivore mammals, including humans. Since fatty acids are not normal dietary constituents, the mechanisms for their absorption into and through the mucosa are more complex, require assistance by enzymes and emulsifiers, and are more susceptible to interindividual variations in transport capacity;

3) Enterally administered free amino acids, acyl aminoacids and their peptidomimetic derivatives are preponderantly metabolized locally at the level of the enterocyte and in the splanchnic bed, so that the time span between their complete absorption into the mucosa and their conversion into the oxidation end-product, $CO_2$, which is the parameter measured by breath tests, is demonstrably shorter than that of fatty acids. In contrast, the oxidative fate of fatty acids, such as octanoate, comprises several more, time dependent steps and takes place in many more organs of the body, such as liver, heart and kidney, and over a longer time span prior to complete conversion into detectable $CO_2$.

Thus, these materials, useful in the method of the invention, have the desirable blending, absorptive and metabolic properties than render them more suitable for application in breath tests for gastric emptying. In effect, they represent a better defined and designed input to the metabolic pathways of gastric emptying, from which it can be reasonably expected that the output function, a measurable metabolic end-product, namely $CO_2$, can be quantitated with greater accuracy and precision than attainable by the application of prior art.

In general, the invention is directed to methods of measuring gastric emptying time comprising providing to a patient a meal comprising a breath test food additive substrate, wherein the substrate is a linear or cyclic acyl aminoacid peptidomimetic that includes a radioactive or non-radioactively labeled carbon atom; having the patient digest the meal so that the carbon labeled nutrients therein are absorbed in the small intestine and metabolized to labeled $CO_2$; and, at periodic intervals, detecting the level of labeled $CO_2$ in breath samples taken from the patient to determine the rate of gastric emptying.

Preferably, the substrate has the characteristics of a compound metabolized by enterocytes and the substrate exhibits zero order absorption from the stomach into the splancnic bed. A linear acyl aminoacid peptidomimetic substrate preferably has R4 equal to acetyl and the R4 group preferably is labeled with $^{13}C$. The preferred substrates are N-acetyl[1-$^{13}C$]-L-leucine and L-2-oxo[$^{13}C$]thiazolidine-4-carboxylic acid. Preferably, the labeled carbon atom in the substrate is non-radioactive and most preferably is $^{13}C$ or $^{11}C$.

The meal fed to the subject in the method of the invention preferably is a microwavable mixture of carbohydrate, protein and fat. For example, the meal can be a microwavable mixture of premeasured amounts of powdered milk; muffin, pancake or custard mix in dried form; grated cheese; and powdered egg or egg substitute.

In aother aspect, the invention is directed to a food adapted to be ingested by a patient in connection with a gastric emptying test, the food comprising carbohydrate, protein and fat; and a breath test food additive substrate, wherein the substrate is a linear or cyclic acyl aminoacid peptidomimetic that includes a radioactive or non-radioactively labeled carbon atom, wherein said food is in a microwavable format.

The invention also includes methods for evaluating the efficacy of a candidate therapeutic agent expected to affect gastrointestinal motility of for assessing a subject's gastrointestinal motility for comparison between healthy and normal parameters. These methods include carrying out the described method for measuring gastric emptying time and then comparing the increase or decrease in breath-testderived emptying time against normative values derived from control subjects with unaided or unimpaired gastric emptying function. In another aspect, the invention is directed to a kit that includes a food adapted to be ingested by a patient in connection with a gastric emptying test, the food comprising carbohydrate, protein and fat, wherein the food is in a microwavable format; and a breath test food additive substrate, wherein the substrate is a linear or cyclic acyl aminoacid peptidomimetic that includes a radioactive or non-radioactively labeled carbon atom. The kit preferably includes a food comprising premeasured amounts of powdered milk; muffin, pancake or custard mix in dried form; grated cheese; and powdered egg or egg substitute, and, further, breath collection sample tubes and a microwavable dish.

BRIEF DESCRIPTION OF THE DRAWINGS

Other features and advantages of the invention will be apparent from the following description of the preferred embodiments thereof and from the claims, taken in conjunction with the accompanying drawings, in which:

FIG. 1 shows a reaction scheme representing a compartmental model for gastric emptying;

FIG. 2 shows linear acyl aminoacid peptidomimetic probes useful in the method of the invention;

FIG. 3 shows cyclic acyl aminoacid peptidomimetic probes useful in the method of the invention;

FIG. 4 is a graph showing results obtained using $^{13}$C-labeled OTZ as a solid phase emptying probe in the method of the invention;

FIG. 5 is a graph showing results obtained using $^{13}$C-labeled OTZ as a liquid phase emptying probe in the (n method of the invention;

FIG. 6 is a graph showing results obtained using [acyl] $^{13}$C-leucine as a liquid phase emptying probe in the method of the invention for determining the effect of motility regulator drugs; and FIG. 7 is a graph showing results obtained using [acyl] $^{13}$C-leucine as a solid phase emptying probe in the method of the invention for determining the effect of disease condition.

DESCRIPTION OF THE PREFERRED EMBODIMENTS OF THE INVENTION

Pharmacologists have come to understand from experimental evidence on mechanisms of drug delivery that the rate and extent of drug absorption after oral administration can be affected by the residence time of the drug in the stomach and along the intestine. The residence time of a drug or food substance in the stomach is dictated to a large extent by two processes: a) dissolution and mixing with stomach contents and b) gastric emptying and gastrointestinal motility. Negligible absorption and metabolism of most drugs and, significantly, no absorption and metabolism of food substances, occurs from the stomach relative to the time of entry into the small intestine. The longer a substance is retained in the stomach prior to delivery via the pylorus to the duodenum, the less likely it is to be absorbed and metabolized within the same time frame as that applicable to a substance that is rapidly emptied from the stomach and subsequently absorbed and metabolized.

Thus, if one is able to quantitate the kinetics of a substance's post-absorptive metabolism, then the rate of gastric emptying can be calculated by mass balance, compartmental modeling, mean residence versus mean input time analysis, and other computational approaches for analyzing the influence of variable gastric emptying on transit rates into the intestine. One such approach depicts the GI tract as two or more serial compartments, the stomach and the small intestine, with absorption and metabolism into the peripheral circulation as kinetic compartments connected to the intestine, as shown in scheme depicted in FIG. 1.

The differential equations resulting from such a model, for example, have been described and validated (Oberle, R. L. and Amidon, G. L. J. Pharmacokinetics & Biopharmaceutics 15:529–543, 1987. Another set of approaches is based on the Wagner-Nelson and Loo-Riegelman data reduction schemes, which when applied to drugs that show instant dissolution (Step B), affords the, rate for gastric emptying, and therefore the. emptying time (i.e. the time span for transfer of drug from Step A to Step C), as a value derived, from solving the rate constant K1 (see Chapter 10, Wagner, J. G. Pharmacokinetics for the Pharmaceutical Scientist, Technomic Publishing Co., Lancaster (Pa.), pp 1–316, 1993).

The system of differential equations implicit in the scheme of FIG. 1 has also been addressed by statistical moment theory based on mean residence time (MAT analysis), when there is prior knowledge of the K3 rate constant, determined independently from a, comparative intravenous administration of drug into Step E, effectively by-passing Steps A through D. Under these circumstances, the gastric emptying time is calculated as the difference between the mean residence time in the body of the drug and/or its metabolites when given by mouth and the commensurate, but shorter, mean residence time obtained when the drug is introduced by intravenous administration (Riegelman, S. and Collier, P. Journal of Pharmacokinetics & Biopharmaceutics, 8:509–534, 1980).

In principle, any drug or other biologically safe molecule can be used as a probe for gastric emptying in accordance with the kinetic formalism exemplified by the scheme of FIG. 1. In practice, however, only certain properties permit any given molecule to serve in this functional role as a marker, especially when admixed with food substances. This latter operational constraint is significant because food meals can trigger physiologic responses that either accelerate or delay gastric emptying. They change properties during digestion and, therefore, potentially affect partition of the probe molecule from the solid food phase into the aqueous phase of the digesta, so that a proportion of the probe will empty with a different K1 value than that which is still embedded in the solid phase.

If a probe molecule is not rapidly absorbed from the duodenum (and jejunum) or is not fully extracted and metabolized within the enterohepatic circulation, the kinetic deconvolution of K2 and K3 will be subject to large inter- and intra-individual variations. These would be attributable to transport and metabolic processes in the course of steps D, E and F and not during the gastric emptying process (Step B). Therefore, imprecision and inaccuracy in the determination of K2 and K3 impinge adversely on the reliable determination for K1 and may render the probe molecule useless as a marker for the gastric emptying process.

Consequently, for application as gastric emptying probes, probe molecules should adhere to the following, and verifiable, profile of molecular properties:

1) Adsorptive and bulk phase behavior. Candidate probe molecules must be able to adhere to the solid phase of a food by adsorbing to proteins and other contained macromolecules without partitioning into any surrounding aqueous phase. In order to facilitate adhesion, candidate probe molecules should be sufficiently polyfunctional so as to adhere by ionic as well as hydrogen bonding to both organic acids and bases and under environments of both low and high polarity, such as those found in the denatured protein component of cooked food substances.

The preferred embodiments for this type of molecule, which also are recognized as safe and compatible with food substances, are the amino acids and in particular their N-acyl, carboxyl ester or amide, and a peptidomimetic derivatives. In contradistinction to simple fatty acids, these molecules are composed of polyfunctional substituents and exhibit amphiphilic behavior when permitted to adhere to either polar or non-polar surfaces, a physicochemical process mediated by the interaction of the lone pair electrons of the amido functionality with the pi-cloud of neighboring acid or ester carbonyls. The synthesis, properties and applications of compounds in this class has been reviewed, as have the numerous tests for their characterization (Mikhalkin, A. P. Russian Chemical Reviews 64:259–275, 1995). The common physical characteristic of these types of molecules is their significantly greater solubility in hot butanol when partitioned against water in comparison to glycine. They also show an aqueous solubility at physiological pH of less than 2 grams per 100 grams of solution.

2) Mucosal absorption behavior. Candidate probe molecules should be rapidly transported across the mucosa of the small intestine in Step C, as well as absorbed through passive processes into the enterocyte. As a class, free amino acids are known to be rapidly absorbed by both sodium dependent and independent transporters, that is, their absorption is facilitated in contrast to that of molecules whose entry into the mucosa is principally passive and diffusive. Also transport of amino acids is maintained during a variety of disease states and is particularly rapid in the fasting state when the metabolic needs of the splanchnic bed are highest for protein synthesis precursor (Gardiner K. and Barbul A., Journal of Enteral and Parenteral Nutrition, 17:277–283, 1993).

The suitability of candidate molecules for use in the method of the invention can be established with in vitro permeability measurements using intestinal sacks and brush border membrane vesicles, as reviewed by Gardner and Barbul (1993) or in cell culture as reviewed by Christensen et al. (1968) (Christensen, H. N., Handlogten, M. E., Lam, I., Tager, H. S. and Zand, R. Journal of Biological Chemistry, 244:1520–1520, 1969). A transport rate less than that of the benchmark substrate N-methyl-aminoisobutyric acid for any candidate probe in the presence of duodenal digestive juice would be evidence of insufficiently rapid transport.

3) Metabolic conversion to $CO_2$. As stated earlier, the principal source of error in the calculation of K1 are the concomitant uncertainties in the determination of K2 and K3. The most suitable candidate molecules as gastric emptying probes, therefore, should be those that exhibit dispositional kinetics which can be measured with greater accuracy by virtue of their biochemical simplicity. The simplest dispositional kinetics are afforded by those molecules which pass from the stomach to the small intestine intact, but then are metabolized preponderantly, if not completely, in the transition between Steps C and E, so that a single metabolite is the species delivered to the peripheral circulation after complete extraction by the splanchnic bed and the liver. An even more preferred subset of candidate probe molecules are those whose metabolism takes place preponderantly at the level of the enterocyte, yielding $CO_2$ as the preponderant, end-stage metabolite.

Thus, if a tracer tag, such as $^{13}C$ or $^{14}C$, is embedded in the candidate molecule so that is is released upon metabolism into $CO_2$, the kinetics of labeled $CO_2$ can then be used to complete the calculations implicit in solving for the mass balance equations underlying the scheme of FIG. 1 and described by the sum of one or two exponential disposition terms, including lag time, and one first order absorption term, also including lag time. Rapid oxidative metabolism is the physiological hallmark of carboxyl labeled aminoacids, especially in the fasted state (Young, V. R., American Journal of Clinical Nutrition, 46:709–725, 1987; Young, V. R. and Ajami, A. M., Journal of Enteral and Parenteral Nutrition) and this phenomenon constrasts starkly with the oxidative metabolism of fatty acids, whose conversion to $CO_2$ is a longer-lived process, proceeding well beyond the metabolic compartments implied in the scheme of FIG. 1.

Moreover, in connection with the suitability of acylated aminoacids and related peptidomimetics, the design of the optimal candidate structure permits the incorporation of the tracer tag into one or more labile, reversible functional groups, such as the N-acyl protecting groups, the protecting and reversible "scaffolding" of the carboxyl group, or similar substituents, as described in Table I. When any such groups are hyrolyzed by intestinal digestive enzymes at Step C or during Step D, and the released group is in turn rapidly metabolized oxidatively in the enterocyte or within the splanchnic bed, the resulting appearance of the tracer tag in the derived $CO_2$ can be subjected to the same analytical formalisms as if the $CO_2$ had arisen from the parent amino acid structure itself. Short chain acyl aminoacids, bearing the tracer tag at the 1-position carbon of the N-acyl group or at the 1 position of a short chain alkyl ester, are exemplars of this class of acylated aminoacid peptidomimetics, among which N-acetyl[-1-$^{13}C$-acetyl]-L-leucine is a most preferred embodiment. This molecule is a substrate for both pancreatic enzymes and enterocytic amidases that are not present in the gastric mucosa and gastric juice.

TABLE I

REVERSIBLE PROTECTING GROUPS

| Modifiable Group | $R^a$ | Reversible Group | $Z^a$ |
|---|---|---|---|
| RC=O | H, Ak, Ar | $RC(OZ)_2$ | Ak |
| | H | $HC(O_2CZ)_2$ | Ak, Ar |
| | H, Ak, Ar | C=C—OZ | Ak |
| | H, Ak, Ar | C=C—$NZ^1Z^2$ | Ak |
| | H | $CHCl(O_2CZ)$ | Ak, Ar |
| | H, Ak, Ar | C=NZ | Ak, Ar, OMe |
| | H, Ak, Ar | 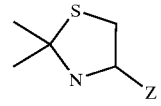 | H, $CO_2Ak$ |
| | H, Ak, Ar | C=C—$O_2CZ$ | Ak, Ar |
| $CO_2H$ | — | $CO_2Z$ | Ak, Ar |
| | — | C=O(SZ) | Ak, Ar |
| | — | C=O($NZ^1Z^2$) | H, Ak, Ar, OH, $NH_2$ |
| | — | $CO_2CHZ^1O_2CZ^2$ | $Z^1$ = H, Ph; $Z^2$ = Ak, Ar |
| | — | $CO_2CHZCl$ | H, Ar |
| | — | $C(OZ)_3$ | Ak |
| | — | $CO_2CO_2Z$ | Ak, Ar |
| | — | $CO_2CH_2Z$ | SMe, SOMe, $SO_2Me$ |
| CONHR | H | $CONHCH_2NZ^1Z^2$ | Ak, Ar |
| | H | $CONHCH_2OH$ | — |

TABLE I-continued

REVERSIBLE PROTECTING GROUPS

| Modifiable Group | $R^a$ | Reversible Group | $Z^a$ |
|---|---|---|---|
| OH | — | $O_2CZ$ | Ak, Ar, … |
| | — | $(-O_3)CZ$ | Ak, Ar, … |
| | — | OZ | Ak, Ar |
| | — | —O—C=C | — |
| | — | $(-O-)_2CZ^1Z^2$ | H, Ak, Ar |
| | — | $O_2CNZ^1Z^2$ | H, Ak, Ar |
| | — | $O_2COZ$ | H, Ak, Ar |
| | — | $O_2CO_2Z$ | H, Ak, Ar |
| | — | $OSiZ_3$ | Ak |
| | — | $(-O)_2CO$ | — |
| | — | $(-O)_3PO$ | — |
| | — | $(-O)_2SO_2$ | — |
| NHR | H, Ak, Ar | NR(C=O)Z | Ak, Ar |
| | H, Ak, Ar | $NRCO_2Z$ | Ak, Ar |
| | H, Ak, Ar | NRC=C | — |
| | H, Ak, Ar | NR(C=O)NHZ | Ak, Ar |
| | Ar | ![succinimide structure: NAr-CH2-N(C=O)(C=O)] | — |
| RN(R)H | H, Ak, Ar | $RN(R)CH_2O_2CZ$ | Ak, Ar |
| SH | — | S(C=O)Z | Ak, Ar |

$^a$Ak, Alkyl; Ar, aryl; adapted from Charton, M. Methods in Enzymology, 112, p. 331 (Table I), 1985

N-acetyl aminoacids, e.g., N-acetyl-cysteine, N-acetyl-glutamine, N-acetyl-methionine and N-acetyl-tyrosine, have been used in the therapeutic practice of clinical nutrition. Their chemical synthesis, physical properties, safety, and high degree of metabolic bioavailabilty is a matter of public record, as described above (Mikhalkin, A. P. Russian Chemical Reviews 64:259–275, 1995).

Among the many possibilities for adherence to the structural preconditions just imposed, the even more preferred gastric emptying probes would be those which can release tracer labeled $CO_2$ directly into the peripheral circulation via purely hydrolytic, rather than oxidative metabolism, during steps C, D and E. Exemplars of this optimal type include tracer labeled carbonates, carbamates, and alkoxycarbonyl peptidomimetic derivatives of suitable amino acids, shown schematically as cyclic aminoacid peptidomimetic probes in FIG. 3, among which L-2-oxo[$^{13}$C]thiazolidine-4-carboxylic acid is the preferred embodiment. This molecule is a substrate for oxoprolinase in the enterocyte and within the enterohepatic circulation, especially the liver.

In practice, candidate tracer probe molecules that meet the criteria imposed in this example can be validated in vitro by determining the rate of release of labeled $CO_2$ in homogenates of intestinal tissue, in homogenates or in intestinal cell line cultures in comparison to the rate of oxidative conversion of octanoic[1-$^{13}$C] acid as the benchmark substrate. Candidate molecules affording a larger per cent of dose as oxidative or hydrolytic tracer release than that obtained with equimolar titers of octanoate, are to be deemed to show suitable metabolic conversion to $CO_2$ for utility as probes in gastric emptying. Validation in vivo is also achieved in a comparative assay using intact mammals by comparing the mean residence time of labeled $CO_2$ derived from an oral bolus of labeled bicarbonate with that of an equimolar amount of candidate probe. Those candidate probes whose mean residence time is least divergent from that of bicarbonate (i.e. within two standard deviations), are to be considered as preferred embodiments.

4) Zero-order emptying kinetics. From the preceding example, a more desirable property for the selection of a suitable gastric emptying probe is its ability to serve as a rapid pro-drug for bicarbonate by virtue of being able to be rapidly converted into bicarbonate at Steps C and D, and prior to Step E in Scheme 1. A further desirable property with regard to providing a more accurate, if not simpler computation of K1, the gastric emptying rate, would be to select candidates whose transfer from steps A to B displays zero-order kinetics. Solution to the differential equations underlying Scheme 1 is facilitated if the transfer of the tracer probe from Step A to B can be described as independent of concentration, that is, as if it has occurred by infusion for a fixed amount of time in contrast to transfer by a first order exponential process.

Under the circumstances of zero-order kinetics, the emptying time becomes equal to the zero order input time and the solution of the equations defining K1 can then be solved with two fewer variables than would be the case for a first order description of the process shown in FIG. 1, inclusive of lag time. Kinetic analysis of the dispositional properties of an oral bolus of either N-acetyl[-$^{13}$C-acetyl]-L-leucine or L-2-oxo[$^{13}$C] thiazolidine-4-carboxylic acid, preferred exemplar cites above, can be demonstrated to meet the requirement of zero order tracer probe transfer from A to C (FIG. 1) by virtue of the goodness of fit shown when the appearance of $^{13}CO_2$ in breath derived from their metabolism is fitted to the zero order (infusion) biexponential functional form.

Use

In accordance with the present invention, the solid food to be checked and swallowed as the meal for a gastric emptying test is in the form of an edible, egg fortified muffin from a microwaveable recipe, freshly prepared prior to use. The base formulation consists of a bulk mix containing 92 grams of powdered, defatted milk; 320 grams of apple flavored instant muffin mix, 80 grams of finely grated Parmesan cheese and 0.6 gram of pulverized L-2-oxo[$^{13}$C] thiazolidine-4-carboxylic acid (OTZ) tracer probe. The mixture is homogenized in a food mill and stored in individual portions of 61.625 grams. Prior to cooking, the individual muffin mix is reconstituted in a microwaveable plastic dish with 110 ml of water and 61 grams of defatted egg substitute and then thoroughly blended and allowed to stand covered for 0.5 hour at room temperature. After shaking well, the mixture is uncovered and microwaved in a 500 watt oven for 4 minutes at medium power, rotated 120 degrees, and again microwaved for 4 minutes. The muffin is loosened around the edges, allowed to cool, and removed from the cooking container.

This preparation is intended to deliver 270 calories, as 35 gr. of carbohydrate, 16 grams of protein and 7 grams of fat together with 125 mg of the tracer dose, which should deliver 1 mg/kg body weight to an 75 kg subject. It may be scaled down proportionately to body weight but preferably not so as to deliver fewer than 250 calories for an adult recipient. Additionally, in order to increase the signal to noise for the detection of $^{13}CO_2$ in breath, the dose of OTZ in the bulk muffin recipe can be increased to 1 gram, so as to deliver approximately 1.67 mg/kg of tracer probe to a 75 kg subject.

To perform a gastric emptying test, the patient fasts overnight, and the next morning a baseline sample of breath is collected in an evacuated serological tube according to the general breath test procedure describe for liquid phase OTZ breath tests (Fukagawa, N. K., Hercules, E. and Ajami, A. M., American Journal of Physiology, 278:E171–176, 2000). The patient then ingests the muffin and drinks 150 ml of water within 10 minutes, at which time the first test breath sample is collected. A second test sample is collected 10 minutes later and thereafter at 20 minute intervals for a total of 200 minutes. It is to be understood that this sampling sequence may be adjusted with fewer or greater samples and over different time spans to accomplish various degrees of greater resolution for either the earlier, ascending portion of the breath test or for determination of the later stages corresponding to the washout period of the tracer probe's postabsorptive metabolism.

The samples are analyzed for isotopic content and corrected for interindividual differences in endogenous $CO_2$ production rate in order to obtain the appropriate data points. A graph showing the results obtained using OTZ as a solid phase emptying probe is depicted FIG. 4. Visual inspection reveals a pronounced shift in the time to peak and apparent "slope" of the rising curve in the test cases.

This pattern, which is consistent with the physiologically normal delay of gastric emptying caused by food, can be further deconvoluted to obtain quantitative values for an emptying rate and other kinetic parameters in accordance with the pharmacokinetic solution to the model described in FIG. 1. These can then be compared to normative data by way of evaluation and any significant deviations from the normal pattern reported as a consequence of pathophysiology or because of the effects caused by therapeutic use of motility regulators. In specific, since the left-most profiles shown in FIG. 4 correspond to subjects whose emptying time is normal, it follows that significant deviation therefrom would indicate a gastric emptying disorder.

The appearance pattern of $^{13}CO_2$ in breath from the OZT control experiments described above shows a sharp rise, that on re-examination with a greater number of sample points, can be demonstrated to follow zero-order absorption kinetics. This is a desirable property in the method of the invention and is attributable to compounds of the acylated aminoacid peptidomimetic class. When OZT is dispensed at 1.5 mg/kg in a 5% glucose solution as the test meal (150 ml) to a normal adult male, as shown in FIG. 5, the OTZ emptying profile in the leftmost curve can be fitted accurately and precisely to a characteristic biexponential zero-order absorption and biexponential disposition equation, inclusive of a lag-time term. Two elderly diabetic patients, but asymptomatic for gastric emptying dysfunction by physical examination, also demonstrated the zero-order biexponential kinetics of OTZ emptying from the stomach, and biexponential metabolism thereafter (as depicted in the middle two curves, open symbols). However, in the diabetic patients, the time to peak, and, therefore the emptying time is shifted to the right of the normal control, confirming that gastroparesis is characteristic of their disease. Lastly, pre-loading the liquid test meal with 10 grams of chocolate toddy syrup containing an additional 4.5 grams of oleic acid in 150 ml of the drink, causes the emptying profile of the normal control to shift even further to the right (rightmost, closed symbols), emulating gastroparesis, as expected since fatty acids and lipids are physiological effectors of delayed emptying. Again, even in this instance, the pattern of absorption and disposition fits the functional equation that defines zero-order absorption kinetics.

The following examples are presented to illustrate the advantages of the present invention and to assist one of ordinary skill in making and using the same. These examples are not intended in any way otherwise to limit the scope of the disclosure.

EXAMPLES

Recommended Embodiments

The first novel probe for gastric emptying useful in the method of the invention is $^{13}C$-labeled N-acetyl-leucine. Pilot experiments have been conducted with four labeling position variants. Referring to FIG. 2, linear acyl aminoacid peptidomimetic probes for use in the method of the invention are preferably labeled in the acyl position (R4). The next preferred labeling position is in either R2 or R3, in the blocking group that is part of R1. The next most preferred labeling position is at the carbonyl carbon in R1. The data from the most appropriate position (R4) are shown in the table below.

Acetyl[$^{13}C$]-L-Leucine 5 mg/kg with liquid test meal (150 ml) or 200 cc muffin

|  | Glucose | Citrate | Oleate | Ensure | Muffin |
| --- | --- | --- | --- | --- | --- |
| n | 5 | 5 | 5 | 5 | 2 |
| Lag | 8 +/− 6 | 7 +/− 7 | 14 +/− 6 | 12 +/− 8 | 16–18 |
| Time to Peak | 34 +/− 10 | 43 +/− 15 | 73 +/− 24 | 87 +/− 14 | 140–160 |
| T1/2 | 17 +/− 5 | 22 +/− 8 | 37 +/− 12 | 44 +/− 7 | 70–80 |

The acyl aminoacid was incorporated into each of four liquid test meals and into a muffin, such as that which was described in the preceding description of use. The appearance of $^{13}CO_2$ in breath after meal ingestion was deconvoluted by fitting the data to the zero-order absorption functional form illustrated in FIG. 5, and the lag time, time to peak and half-emptying time, T1/2 (defined as lag time plus time to peak divided by 2) were calculated for each test subject and reported as the mean of the trials conductated (given as n). Glucose and citrate test meal drinks afforded characteristic gastric emptying statistics, consistent with the literature for drinks of similar caloric content as osmolarity. Increasing both the osmolarity and complexity of the meal, as for example, by the addition of oleate or by substituting the drink with a ntriglyceride and electrolyte rich enteral hyperalimentation formula, such as the clinical nutrition product Ensure®, shifted the half emptying time to significantly higher values, again as predicted in the literature. In a solid phase emptying experiment, the gastric emptying of the solid meal muffin, characterized by the breath test kinetics of N-acetyl[1-$^{13}C$-acetyl]-L-leucine, showed the longest half-emptying time. This was again consistent with normative values for normal emptying of a solid meal and recapitulated the quantitative findings for the use of L-2-oxo[$^{13}C$]thiazolidine-4-carboxylic acid, as illustrated in FIG. 4. The performance of the leucine-based peptidomimetic materials, therefore, can be seen to conform to the expectations of increased emptying times with increasing meal complexity.

Another amino acid based probe, useful in the method of the invention, having similar economics, technical practicality, physical adsorptive properties, and absorption kinetics to N-acetyl[1-$^{13}C$-acetyl]-L-leucine is the novel gastric emptying substrate oxothiazolidine-4-carboxylic acid (OTZ). This compound is a cysteine pro-drug that releases carbon dioxide when metabolized by oxoprolinase. Oxoprolinase is present in most body tissues, and abundant in the liver and gut, including the enterocyte and surrounding tissues. This probe has been tested similarly to the acetyl-leucine material, with data as shown below.

2-[$^{13}$C -OTZ
1.5 mg/kg with liquid test meal (150ml) or 200 cc muffin

|  | Water | 5% Glucose | Ensure | Muffin |
|---|---|---|---|---|
| n | 30 | 10 | 5 | 5 |
| Lag (metab) | 7 +/− 9 | 8 +/− 7 | 10 +/− 4 | 12 +/− 6 |
| Time to Peak | 38 +/− 8 | 42 +/− 6 | 92 +/− 10 | 150 +/− 18 |
| T1/2 | 19 +/− 4 | 21 +/− 3 | 46 +/− 5 | 75 +/− 9 |

The results of the emptying breath test with this cyclic peptidomimetic probe were again consistent with the nature of the meal and the findings from both literature and the preceding example with a related linear acyl peptidomimetic as the breath test substrate.

Technical Validation

After both proposed materials were demonstrated to conform to expectation (e.g. increased half emptying time and delayed emptying with increased caloric, fat, and fiber content), the acetyl leucine material was tested in two validation platforms. One validation platform administered the substrate with a meal containing microspheres that are visible with abdominal tomography. The second validation platform provided for simultaneous admnistration of the substrate with Technitium-sulfur colloid according to a scintigraphy protocol. With both validations, the performance of the substrate was highly correlated with the independent measures as demonstrated by the following linear regressio equations which were derived experimentally from breath tests experiments, conducted as above using both liquid and solid meals in 10 normal control subjects:

ACETYL LEUCINE (AL) vs. MICROSPHERES (MS)

Liquid meal AL=1.16 (±0.17)×MS−23 (±5)

R=0.87 (p<0.01)

ACETYL LEUCINE (AL) vs. Tc–S (TC)

Solid meal AL=0.93 (±0.12)×TC+16 (±7)

R=0.85 (p<0.01)

The latter validation was repeated for comparison purposes with free octanoic acid as the substrate. The material disclosed in this patent application was more highly correlated with the gold standard of scintigraphy.

OCTANOATE (OCT) vs. Tc–S (TC)

Solid meal OCT=0.85 (±0.22)×TC+26 (±17)

R0.72 (p<0.05)

Demonstrations for Substrate Use as Therapy Monitors

Two experiments were conducted to demonstrate the utility of the substrates in drug evaluation and disease assessment. In the first demonstration, the substrate was given with a liquid test meal with drugs known to accelerate or delay gastric emptying. In FIG. 6 summarizing this experiment, metoclopramide is shown as a prokinetic agent. Similarly, loperamide is shown to delay emptying. Metoclopramide accelarated the gastric emptying profile in a statistically significant manner, while loperamide afforded emptying times trending toward greater than normal half-emptying values and significantly longer than those induced by metoclopramde.

In the second demonstration, the substrate was given in a solid meal to study subjects with disease known to slow gastric emptying. Both the gastro-esophageal reflux (GERD) and the chronic liver disease subjects demonstrated statistically significant slower gastric emptying in a solid meal (muffin) experiment, as shown in FIG. 7.

Reference

Bjorkman D J. Moore J G. Klein P D. Graham D Y. 13C-bicarbonate breath test as a measure of gastric emptying *American Journal of Gastroenterology*. 86(7):821–3, 1991 July.

Brained B. Adams S. Duane L P. Ort K H. Maul F D. Lembcke B. Hor G. Caspary W F. The [13C]acetate breath test accurately reflects gastric emptying of liquids in both liquid and semisolid test meals. *Gastroenterology*. 108(4):1048–55, 1995 April.

Campbell I W. Heading R C. Tothill P. Buist T A. Ewing D J. Clarke B F. Gastric emptying in diabetic autonomic neuropathy. *Gut*. 18(6):462–7, 1977 June.

Charles F. Camilleri M. Phillips S F. Thomforde G M. Forstrom L A. Scintigraphy of the whole gut: clinical evaluation of transit disorders [see comments]. [Journal Article] *Mayo Clinic Proceedings*. 70(2):113–8, 1995 February.

Choi M G. Camilleri M. Burton D D. Zinsmeister A R. Forstrom L A. Nair K S. Reproducibility and simplification of 13C-octanoic acid breath test for gastric emptying of solids. *American Journal of Gastroenterology*. 93(1):92–8, 1998 January.

Choi M G. Camilleri M. Burton D D. Zinsmeister A R. Forstrom L A. Nair K S. [13C]octanoic acid breath test for gastric emptying of solids: accuracy, reproducibility, and comparison with scintigraphy. *Gastroenterology*. 112 (4):1155–62, 1997 April.

Farrell F J. Keeffe E B. Diabetic gastroparesis. [Review][83 refs] [Journal Article. Review. Review, Academic] *Digestive Diseases*. 13(5):291–300, 1995 September–October.

Fisher R S. Malmud L S. Scintigraphic techniques for the study of gastrointestinal motor function. [Review] [72 refs] [Journal Article. Review] *Advances in Internal Medicine*. 31:395–418, 1986.

Galati J S. Holdeman K P. Bottjen P L. Quigley E M. Gastric emptying and orocecal transit in portal hypertension and end-stage chronic liver disease. [Journal Article] *Liver Transplantation & Surgery*. 3(1):34–8, 1997 January.

Gordon F. Munoz R. Villarreal J. Gonzalez-Montesinos F. Lifshitz A. Cervantes L. Advances in gastric emptying studies by means of computerized scintigraphy. [Journal Article] *Archivos de Investigacion Medica*. 11(3):393–408, 1980.

Holt S. Cervantes J. Wilkinson A A. Wallace J H. Measurement of gastric emptying rate in humans by real-time ultrasound. [Journal Article] *Gastroenterology*. 90(4):918–23, 1986 April.

House A. Champion M C. Chamberlain M. National survey of radionuclide gastric emptying studies. *Canadian Journal of Gastroenterology*. 11(4):317–21, 1997 May–June.

Konturek J W. Fischer H. van der Voort I R. Domschke W. Disturbed gastric motor activity in patients with human immunodeficiency virus infection. [Journal Article] *Scandinavian Journal of Gastroenterology*. 32(3):221–5, 1997 March.

Lundell L. Myers J C. Jamieson G G. Is motility impaired in the entire upper gastrointestinal tract in patients with gastro-oesophageal reflux disease?. [Journal Article] *Scandinavian Journal of Gastroenterology*. 31 (2):131–5, 1996 February.

Maughan R J. Leiper J B. Methods for the assessment of gastric emptying in humans: an overview. [Review] [22 refs] [Journal Article. Review. Review, Tutorial] *Diabetic Medicine*. 13(9 Suppl 5):S6–10, 1996 September.

Maes B D. Ghoos Y F. Rutgeerts P J. Hiele M I. Geypens B. Vantrappen G. [*C]octanoic acid breath test to measure gastric emptying rate of solids. *Digestive Diseases & Sciences*. 39(12 Suppl):104S–106S, 1994 December.

Mossi S. Meyer-Wyss B. Beglinger C. Schwizer W. Fried M. Ajami A. Brignoli R. Gastric emptying of liquid meals measured noninvasively in humans with [13C]acetate breath test. Digestive Diseases & Sciences. 39(12 Suppl):107S–109S, 1994 December.

Poitras P. Picard M. Dery R. Giguere A. Picard D. Morais J. Plourde V. Boivin M. Evaluation of gastric emptying function in clinical practice. [Journal Article] *Digestive Diseases & Sciences*. 42(11):2183–9, 1997 November.

Vantrappen G. Methods to study gastric emptying. *Digestive Diseases & Sciences*. 39(12 Suppl):91S–94S, 1994 December.

What is claimed is:

1. A method of measuring gastric emptying time comprising: providing to a patient a meal comprising a breath test food additive substrate, wherein said substrate is a linear acyl aminoacid peptidomimetic that includes a radioactive or non-radioactively labeled carbon atom, and wherein said substrate is selected from the group consisting of:

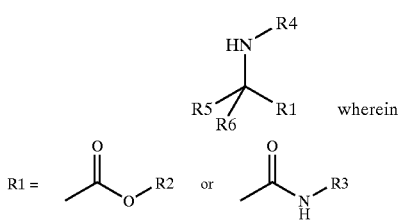

where
  R2=H, methyl, ethyl, propyl, butyl, pentyl, hexyl, isopropyl, isobutyl, sec-butyl tert-butyl, isopentyl, isohexyl, phenyl, phenylmethyl; and
  R3=H, methyl, ethyl, propyl, butyl, pentyl, hexyl, isopropyl, isobutyl, sec-butyl tert-butyl, isopentyl, isohexyl, phenyl, phenylmethyl, R4=acetyl;
  R5=H, methyl, ethyl, propyl, butyl, pentyl, hexyl, isopropyl, isobutyl, sec-butyl tert-butyl, isopentyl, isohexyl, phenyl, phenylmethyl; and
  R6=H, if R5≠H; CH2-OH, CH2-SH, CH2-CH2-CH2-OH, CH2-CH2-S—CH3, CH2-COOR2, CH2-CH2-COOR2, CH2-CH2-CH2-COOR3, CH2-CH2-CON—R3, CH2-CH2-CH2-NH2, or CH2-CH2-CH2-CH2-NH2 having said patient digest said meal so that the carbon labeled nutrients therein are absorbed in the small intestine and metabolized to labeled $CO_2$; and detecting the level of $CO_2$ in breath samples taken from the patient at periodic intervals to determine the rate of gastric emptying.

2. A method of measuring gastric emptying time comprising: providing to a patient a meal comprising a breath test food additive substrate, wherein said substrate is a linear acyl aminoacid peptidomimetic that includes a non-radioactively labeled carbon atom, and wherein said substrate is selected from the group consisting of:

where
  R2=H, methyl, ethyl, propyl, butyl, pentyl, hexyl, isopropyl, isobutyl, sec-butyl tert-butyl, isopentyl, isohexyl, phenyl, phenylmethyl; and
  R3=H, methyl, ethyl, propyl, butyl, pentyl, hexyl, isopropyl, isobutyl, sec-butyl tert-butyl, isopentyl, isohexyl, phenyl, phenylmethyl, R4=formyl, acetyl, enzoyl, benzyloxycarbonyl, t-butoxycarbonyl, butyryl, ethoxycarbonyl, hippuryl, isopropyloxycarbonyl, methoxyacetyl, methoxycarbonyl, pivaloyl, propionyl,
  wherein R4 is labeled with $^{13}C$;
  R5=H, methyl, ethyl, propyl, butyl, pentyl, hexyl, isopropyl, isobutyl, sec-butyl tert-butyl, isopentyl, isohexyl, phenyl, phenylmethyl; and
  R6=H, if R5≠H; CH2-OH, CH2-SH, CH2-CH2-CH2-OH, CH2-CH2-S—CH3, CH2-COOR2, CH2-CH2-COOR2, CH2-CH2-CH2-COOR3, CH2-CH2-CON—R3, CH2-CH2-CH2-NH2, or CH2-CH2-CH2-CH2-NH2 having said patient digest said meal so that the carbon labeled nutrients therein are absorbed in the small intestine and metabolized to labeled $CO_2$; and detecting the level of $CO_2$ in breath samples taken from the patient at periodic intervals to determine the rate of gastric emptying.

3. A method of measuring gastric emptying time comprising:
  providing to a patient a meal comprising a breath test food additive substrate, wherein said substrate is N-acetyl [1-$^{13}C$]-L-leucine, having said patient digest said meal so that the carbon labeled nutrients therein are absorbed in the small intestine and metabolized to labeled $CO_2$; and detecting the level of $CO_2$ in breath samples taken from the patient at periodic intervals to determine the rate of gastric emptying.

4. A method of measuring gastric emptying time comprising:
  providing to a patient a meal comprising a breath test food additive substrate, wherein said substrate is L-2-oxo

[$^{13}$C] thiazolidine-4-carboxylic acid, having said patient digest said meal so that the carbon labeled nutrients therein are absorbed in the small intestine and metabolized to labeled $CO_2$; and detecting the level of $CO_2$ in breath samples taken from the patient at periodic intervals to determine the rate of gastric emptying.

* * * * *

UNITED STATES PATENT AND TRADEMARK OFFICE
CERTIFICATE OF CORRECTION

PATENT NO. : 6,740,305 B1  
APPLICATION NO. : 09/958438  
DATED : May 25, 2004  
INVENTOR(S) : Alfred M. Ajami Page 1 of 1

It is certified that error appears in the above-identified patent and that said Letters Patent is hereby corrected as shown below:

On the title page item (73), Assignee's name should read --XANTHUS LIFE SCIENCES, INC.--

Signed and Sealed this

Tenth Day of April, 2007

JON W. DUDAS  
*Director of the United States Patent and Trademark Office*